(12) United States Patent
Gebauer

(10) Patent No.: US 11,402,357 B2
(45) Date of Patent: Aug. 2, 2022

(54) CONTAINERS FOR CHROMATOGRAPHY MEDIA

(71) Applicant: Cytiva Sweden AB, Uppsala (SE)

(72) Inventor: Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 824 days.

(21) Appl. No.: 15/208,361

(22) Filed: Jul. 12, 2016

(65) Prior Publication Data

US 2016/0320358 A1    Nov. 3, 2016

Related U.S. Application Data

(62) Division of application No. 13/518,509, filed as application No. PCT/EP2010/007830 on Dec. 21, 2010, now Pat. No. 9,421,479.

(60) Provisional application No. 61/370,878, filed on Aug. 5, 2010.

(51) Int. Cl.
| | |
|---|---|
| *G01N 30/56* | (2006.01) |
| *B01D 15/20* | (2006.01) |
| *B01D 15/22* | (2006.01) |
| *G01N 30/60* | (2006.01) |
| *C07K 1/14* | (2006.01) |
| *C07K 1/18* | (2006.01) |
| *C07K 1/20* | (2006.01) |
| *C07K 1/22* | (2006.01) |

(52) U.S. Cl.
CPC .......... *G01N 30/56* (2013.01); *B01D 15/206* (2013.01); *B01D 15/22* (2013.01); *C07K 1/14* (2013.01); *C07K 1/18* (2013.01); *C07K 1/20* (2013.01); *C07K 1/22* (2013.01); *G01N 30/6069* (2013.01); *G01N 2030/562* (2013.01)

(58) Field of Classification Search
CPC .............. G01N 30/56; G01N 30/6069; G01N 2030/562; B01D 15/206; B01D 15/22; C07K 1/14; C07K 1/18; C07K 1/20; C07K 1/22
See application file for complete search history.

(56) References Cited

U.S. PATENT DOCUMENTS

| | | | |
|---|---|---|---|
| 3,430,815 A | 3/1969 | Weimer et al. | |
| 4,250,035 A | 2/1981 | McDonald et al. | |
| 4,496,461 A | 1/1985 | Leeke et al. | |
| 4,676,898 A | 6/1987 | Saxena | |
| 5,021,162 A * | 6/1991 | Sakamoto | B01D 15/206 210/198.2 |
| 5,350,513 A | 9/1994 | Markowitz | |
| 5,667,676 A | 9/1997 | Maska | |
| 6,936,166 B1 | 8/2005 | Salven et al. | |
| 2004/0182789 A1* | 9/2004 | Gill | B01D 15/22 210/656 |
| 2006/0124525 A1* | 6/2006 | Bellafiore | B01D 15/22 210/198.2 |
| 2007/0219524 A1* | 9/2007 | Burnout | A61J 1/10 604/408 |

(Continued)

*Primary Examiner* — Benjamin L Lebron
(74) *Attorney, Agent, or Firm* — Eversheds Sutherland (US) LLP

(57) ABSTRACT

The invention relates to containers or bags for chromatographic media and methods of packing chromatography columns using such containers. The bags may be used for storing and/or transporting chromatographic media and can be inserted directly into the chamber of a chromatography column in readiness for use.

4 Claims, 7 Drawing Sheets

(56) References Cited

U.S. PATENT DOCUMENTS

2008/0217248 A1\* 9/2008 Gebauer .............. B01D 15/206
   210/656

\* cited by examiner

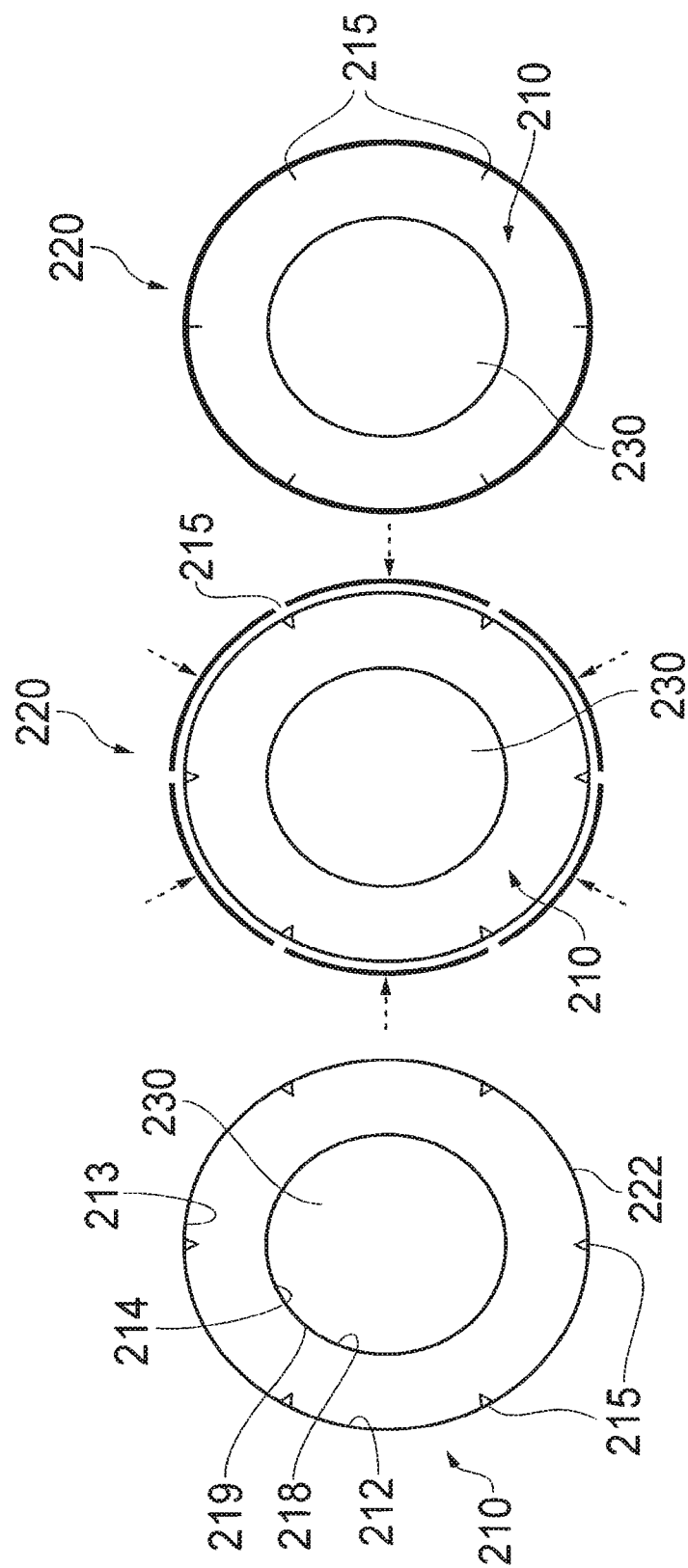

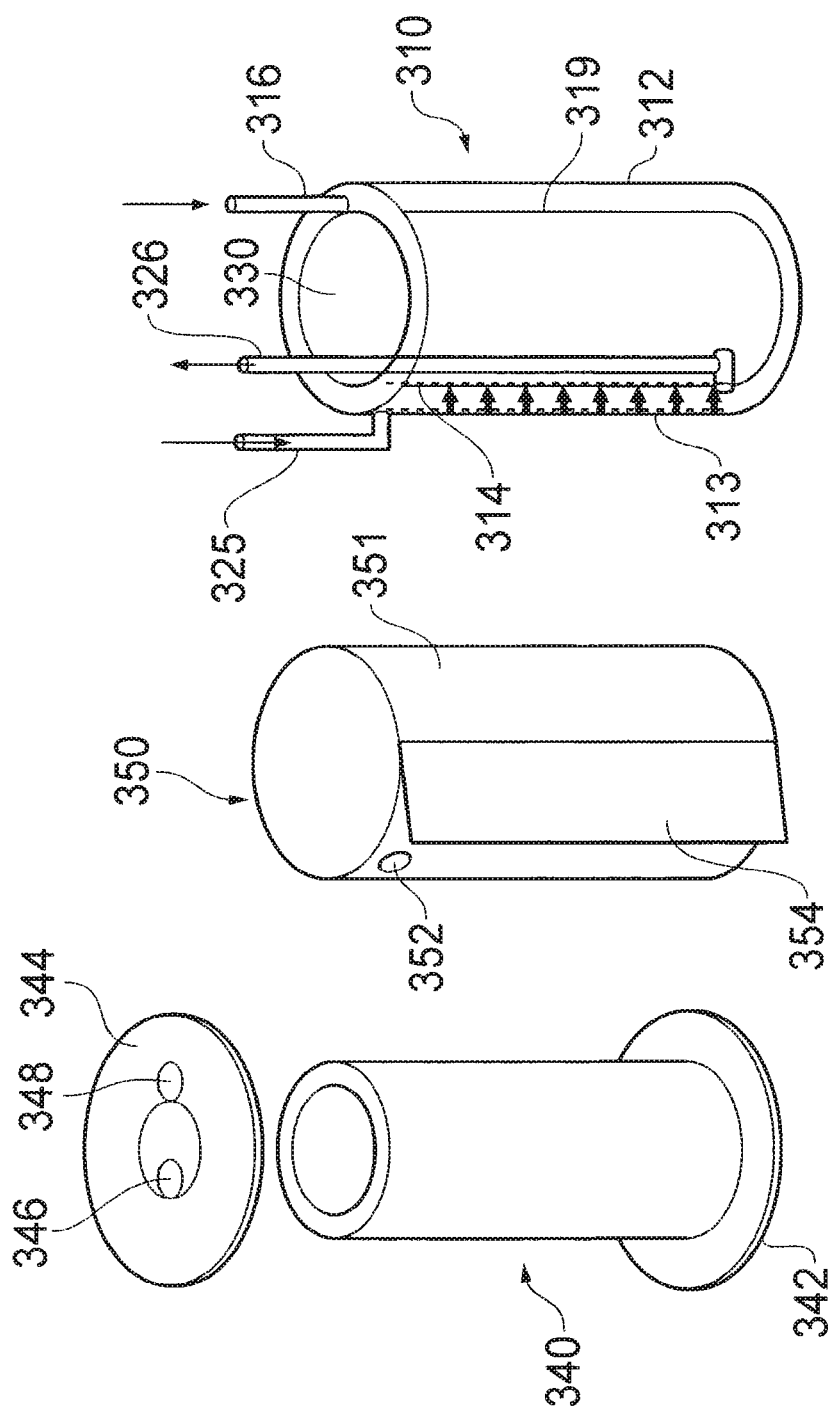

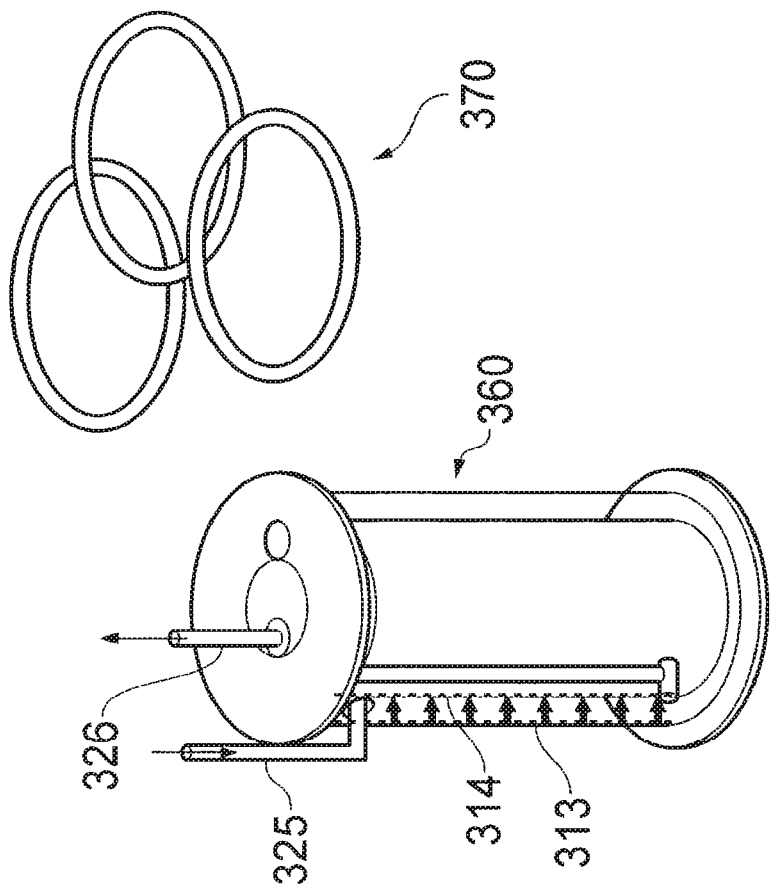
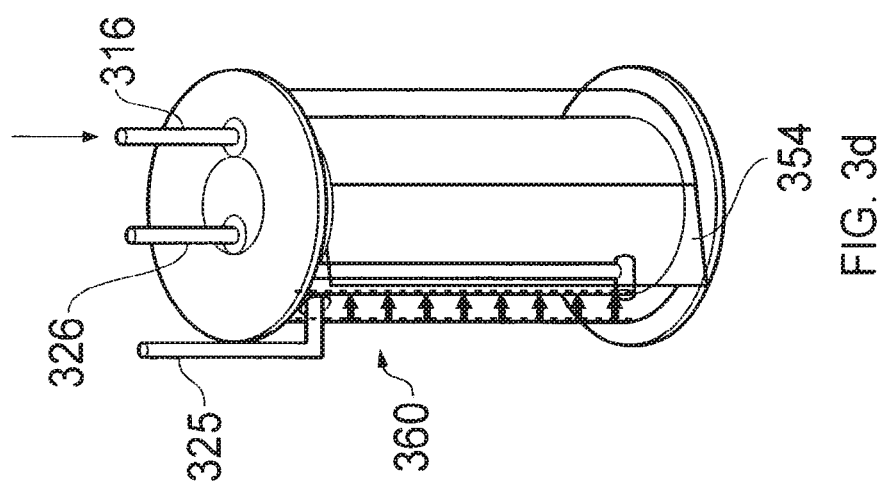

CONTAINERS FOR CHROMATOGRAPHY MEDIA

CROSS-REFERENCE

Field of the Invention

The invention relates to the separation of chemical compounds by column chromatography. In particular, the invention relates to containers or bags for chromatographic media and methods of packing chromatographic columns or preparing consolidated beds of chromatographic media using such containers.

BACKGROUND

Columns used in liquid chromatography typically comprise a tubular or cylindrical body enclosing a packed bed of porous chromatography medium through which a carrier liquid flows, with separation taking place by partitioning between the carrier liquid and solid phase of the porous medium. Cylindrical columns are generally known as 'axial' columns, chromatographic separation typically occurring in a vertical direction down the length of the column, while tubular columns are generally known as 'radial' columns with separation taking place in a radial direction as the carrier liquid flows to the centre of the cylinder.

Prior to any separation process, the bed has to be prepared by starting from the particulate medium that is to be introduced into the column. Conventional columns aimed for high efficiency separations deploy a process of bed formation, which is called 'the packing procedure'. In high efficiency separations, a correctly packed bed is a critical factor influencing the performance of a column containing a packed bed. Typically, the packed bed is prepared by slurry packing, i.e., consolidating a suspension of discrete particles or fibres in liquid, known as slurry that is pumped, poured, or sucked into the column. Once the predetermined volume of slurry has been delivered into the column it needs to be further consolidated and compressed.

In axial columns or in axial chromatography, the slurry can be compressed by moving a movable adapter down the longitudinal axis of the column towards the bottom of the column, normally at a constant speed. The excess liquid during this procedure is expelled at the column outlet, while the media particles are retained by means of a filter material, a so-called 'bed support' or 'frit', with pores too small to allow the media particles to pass though. The packing process is complete once the packed bed has been compressed by the optimum degree of compression.

Another approach for column slurry packing used both in axial and radial columns is the flow packing method, where compression of the porous structure is primarily achieved by applying a high flow rate over the column, thereby forming a porous structure starting at the outlet bed support. The resulting drag force on the particles in the porous structure causes eventually a pressure drop and a compression of the bed. The compressed bed is finally confined by bringing the adapter into position. Presently, only flow packing methods are known for packing radial columns.

The efficiency of subsequent chromatographic separation relies strongly on 1) the liquid distribution and collection system at the fluid inlet and outlet of the packed bed, 2) the special orientation (also know as the packing geometry) of the media particles in the packed bed, and 3) the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such overcompressed beds can affect throughput and binding capacity, and, in general, give much higher operating pressures. If the compression is optimum, then the separation peaks formed during use exhibit much less leading or tailing and are substantially symmetrical. The optimum degree of compression is also crucial for achieving good long-term stability of the porous structure, thereby securing optimal performance throughout a number of process cycles. The optimum degree of compression required for a column is determined experimentally for each column size (width or diameter), bed height, and media type.

An alternative packing method used for axial columns is called "dry packing", where the column is filled with dry particles of the porous medium and liquid is introduced in the column afterwards. This has advantages in prepacked columns that can be delivered dry to the customer without having to add any preservatives to the packing liquid and minimizing weight during transport. Dry packing is typically used for silica media aimed at separation of small molecules, as described e.g. by G Guiochon J Chromatogr A 704 (1995) 247-268, although fairly poor column efficiencies are obtained. For swellable chromatography media, such as dextran or agarose-based media commonly used in separation of biomolecules, dry packing has however been avoided due to a perception that the swelling of the particles will cause poor performance of the packed bed.

The above described background for preparation of packed beds adapted for high efficiency chromatographic separations applies equally to packed beds or fixed beds aimed for achieving bio-reactions such as enzymatic conversions, the treatment of cells or the growth and cultivation of cells adherent to the packed bed with high efficiency.

The columns and packed beds described above may also be used for stabilisation of substances and in particular biomolecules such as proteins, antibodies and cells. This stabilistation may improve and facilitate storage and transport of the molecules, for example. The binding of substances, particularly biomolecules, to chromatography media may preserve activity and stability of the substance more than is achievable with other concentration methods such as filtration, precipitation or freeze-drying.

Technical Problem

There are a number of problems associated with existing methods for preparing and packing columns. Media is generally shipped to operators in large containers and must be carefully weighed out and transferred to columns in preparation for the packing procedure. This can be a time-consuming, wasteful and expensive process as it involves a trained technician as much of the media is not used and must be stored. Where the media are to be used in the preparation of approved products, such as drugs and foodstuffs, regulatory requirements must also be satisfied. Sterilisation and cleaning of the media and/or column to reduce microbial load can prove difficult for users. Furthermore, the columns are often complex and have a large footprint in order to carry out the packing procedure.

Another problem is that columns known in the prior art are not suitable for the stabilisation of substances for the purpose of storage and transport due to high cost, complexity and low flexibility. There is therefore a need to provide a simple and cost-efficient device and method for accomplishing a stabilisation of substances through the process of adsorption to a chromatography medium and desorption prior to further processing or use.

It is an object of the present invention to mitigate the aforementioned problems associated with prior art methods of packing columns and stabilising substances for storage and transport.

SUMMARY OF THE INVENTION

In a first aspect of the present invention, there is provided a flexible bag for chromatographic medium, said bag comprising an exterior wall of a non-porous material attached to a first liquid distribution element and a second liquid distribution element thereby defining a compartment for chromatographic medium therein; said first liquid distribution element being opposed to said second liquid distribution element; and a medium filling port; optionally comprising a first and a second end piece attached to said exterior wall and adjacent to the first and second liquid distribution element respectively, both said end pieces comprising an opening for receipt of an inlet or an outlet for carrier liquid; wherein the first liquid distribution element and/or the second liquid distribution element are welded or moulded to said wall.

In one aspect, the bag has a tubular configuration and additionally comprises an interior wall, wherein the first liquid distribution element is welded or moulded to said exterior wall and the second liquid distribution element is welded or moulded to said interior wall. Preferably, the bag is for use in radial chromatography.

In another aspect, the bag has a cylindrical configuration and comprises a first and a second end piece attached to the exterior wall and adjacent to the first and second distribution element respectively, both said end pieces comprising an opening for receipt of an inlet or outlet for carrier liquid.

In a further aspect, the first and second end piece are welded or moulded to the exterior wall. Preferably, the first and second end piece are made from a rigid or semi-rigid material. Suitable materials include inert metals or plastics.

In one aspect, the first liquid distribution element and the second liquid distribution element is selected from the group consisting of filter, mesh and net. Preferably, the distribution element is a woven, mesh, filter and sinter.

In another aspect, the first liquid distribution element and the first end piece are an integrated unit, and the second liquid distribution element and the second end piece are an integrated unit. The integrated unit may be formed, for example, by moulding or machining. Suitably, the first end piece portion is made from polypropylene.

In a further aspect, the bag is for use in axial chromatography.

In one aspect, the bag additionally comprises a second compartment having an inlet for hydraulic fluid.

In another aspect, the wall or film is made from a plastic polymeric material, in particular materials which are for welding or moulding. Plastic polymers based upon polyethylene are particularly suitable. Thus suitable walls or films include, for example, American Renolit Infuflex Barrier 9101 (SOLMED®. BF 9101; American Ronolit Crop, La Porte, Ind., USA), American Renolit BF-1400 (.SOLMED® BF-1400 Film; American Renolit Corp, La Porte, Ind., USA), American Renolit 4301 (SOLMED® Granuflex, American Renolit Crop, La Porte, Ind., USA), Mitos Durapure (Mitos Technologies, Phoenixville, Pa., USA) and MILLIPORE® Pureflex Process Container Film, (Millipore Corp, Billerica, Mass., USA).

In a further aspect, the bag additionally comprises a semi-rigid or rigid housing around the wall to provide rigidity in an axial and/or radial direction.

In one aspect, the bag additionally contains wet or dry chromatographic medium. In a preferred aspect, the wet or dry chromatographic medium is sterile. The bag can be sterilised by treatment with radiation, autoclaving or chemical disinfectants. Gamma radiation is particularly effective. Milder treatments can also be used to reduce the microbial load, or total number of microbes such as bacteria and fungi present in the medium.

In a second aspect of the present invention, there is provided a method of packing a chromatography column, said method comprising the steps of
  a. inserting a bag as hereinbefore described into a chamber of a chromatography column;
  b. closing the column housing; and
  c. forming or compressing a packed bed or a consolidated bed or a fluidised bed of chromatographic medium.

The consolidated bed is here defined as a porous structure of a bed of chromatography medium in the absence of a substantial mechanical compression. A consolidated bed is for example formed by applying a downward fluid flow to an axial chromatography column filled with a suspension of chromatography medium. Hereby, a porous consolidated bed is formed at the outlet of the column (at the filter) until all chromatography medium has been settled. Such a consolidated bed can be used to achieve a binding of a chemical substance, such as a protein, peptide, antibody, nucleic acid or other biological molecule. The consolidated bed can also be used to bind cells.

The top end piece/filter may be fixed (gap formation) or moved towards or close to the surface of the consolidated bed to reduce the hold-up volume and gap, respectively.

One aspect of the invention is to provide a flexible container for a consolidated bed where one or a plurality of flexible walls are mechanically supported by a rigid housing for providing rigidity when applying fluid pressure to the interior space of the container and the consolidated bed.

Another aspect of the invention is to provide a flexible container that contains chromatography medium and where flexible container with its content can be frozen after having loaded the chromatography medium with a chemical.

Another aspect of the invention is to provide a flexible container filled with chromatography medium that can be frozen, thawed and used to form a consolidated bed from the chromatography medium in order to apply further process steps involving the application of liquid to said consolidated bed.

In one aspect, the bag contains dry chromatographic medium and said packed bed is formed by adding liquid to swell said medium to give a swollen volume Vs in a liquid of about 105-120% of the column chamber. The term "swollen volume (Vs)" as used herein means the sediment volume of an aliquot of particles suspended and equilibrated in a liquid. The sediment volume can be measured by suspending the aliquot of particles, equilibrating for up to 24 hours, resuspending the particles if needed, letting the particles sediment and measuring the sediment volume in a graded vessel such as a measuring cylinder.

In another aspect, the bag contains wet medium, the column housing is rigid and the packed bed is formed or compressed by axial compression of the bag.

In a further aspect, the column comprises a hydraulic chamber and the packed bed is formed or compressed by filling said chamber with a hydraulic fluid. The hydraulic chamber may be a flexible bag. In one aspect, the bag may comprise a second compartment and the packed bed is formed or compressed by filling said second compartment with a hydraulic fluid.

Optionally, the column comprises a movable piston or adapter and the packed bed is formed or compressed by axial movement of said piston or adapter.

In one aspect, the bag containing wet medium is placed over a rigid core within the column chamber and the packed bed is formed or compressed by radial compression of the bag. Preferably, the packed bed is formed or compressed by radial compression of the column housing. In one aspect, radial compression of the column housing is effected by tightening radial bands on the outside of the housing.

In another aspect, the volumetric compression of the wet medium is 5 to 20%. Preferably the volumetric compression is 7.0 to 15%.

In a further aspect, the method additionally comprises sterilising the column with radiation, such as gamma radiation. Similar treatments can be used to reduce the microbial load.

In one aspect, a consolidated or a fluidised bed of chromatographic medium is formed, the method additionally comprising the steps of d) loading a chemical or a cell onto said consolidated bed or fluidised bed; and e) removing said bag from said chamber of said chromatography column for storage and/or transport. In a preferred aspect, the chemical is selected from the group consisting of protein, antibody, peptide, oligopeptide, nucleic acid, oligonucleotide, RNA, DNA, oligosaccharide and polysaccharide.

In another aspect, the method additionally comprising the step of storing and/or transporting the bag. The bag is stored and/or transported at a temperature between −20° C. and 20° C.

In a further aspect, the method additionally comprising the step of returning the bag to the chromatography column and eluting said chemical or cell from said consolidated bed or fluidised bed. In a preferred aspect, the chemical is selected from the group consisting of protein, antibody, peptide, oligopeptide, nucleic acid, oligonucleotide, RNA, DNA, oligosaccharide and polysaccharide.

In a third aspect of the present invention, there is provided a use of a bag according to the first aspect of the invention for storing and/or transporting a chemical or a cell loaded onto wet or dry chromatographic medium. In one aspect, the bag is stored and/or transported at a temperature between −20° C. and 20° C. centigrade.

In a fourth aspect of the present invention, there is provided a chromatograpy column comprising a flexible bag as hereinbefore described.

According to a fifth aspect of the present invention, there is provided a use of a chromatography column as hereinbefore described for separating or purifying or processing a chemical or a cell. In a preferred aspect, the chemical is selected from the group consisting of protein, antibody, peptide, oligopeptide, nucleic acid, oligonucleotide, RNA, DNA, oligosaccharide and polysaccharide. Preferably,

BRIEF DESCRIPTION OF THE DRAWINGS

FIGS. 2a, b and c are schematic sectional plan views of a cartridge containing a bag in accordance to the invention which can be packed by radial compression.

FIGS. 3a, b and c are schematic diagrams illustrating the component parts of a column which contains a bag according to the invention which can be packed by radial compression. FIGS. 3d and e illustrate how the component parts are fitted together and operate.

DETAILED DESCRIPTION OF THE DRAWINGS

Figure 1B:
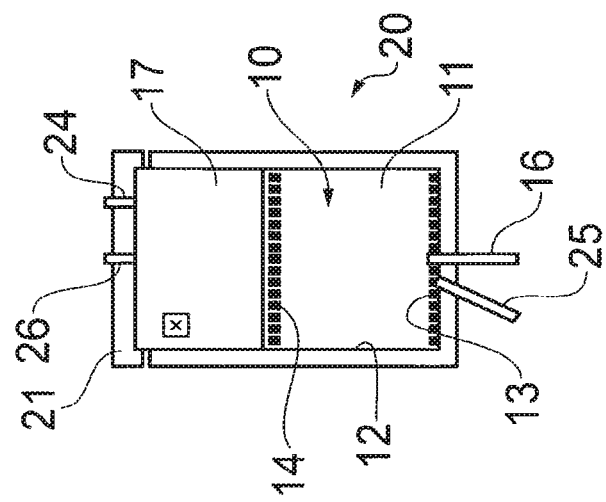
FIGS. 1a and 1b show schematic, sectional views of one embodiment of a welded bag (10) according to the invention that has a semi-ridged housing that can be packed by axial compression.
Figure 1A:
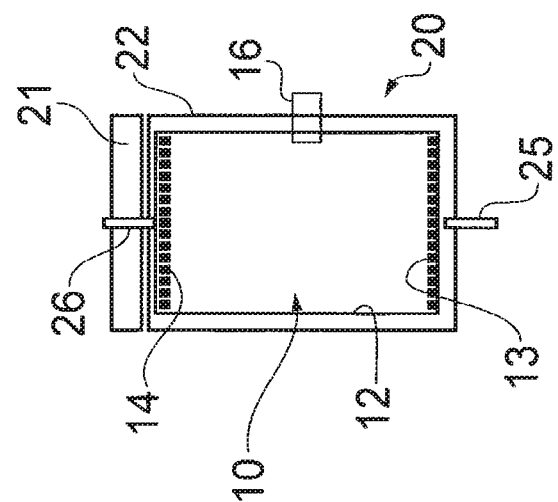

FIGS. 1a and 1b show schematic, sectional views of one embodiment of a welded bag (10) according to the invention placed in a column (20). The bag (10) consists of a first (13) and a second (14) liquid distribution element welded to a wall (12) of a non-porous material. The distribution elements (13, 14) are bed supports or frits or nets or sinters which act as filters, having pores that are too small to allow chromatographic media to pass through but are porous to liquids. The non porous material or film is made of a plastic polymer, those based upon polyethylene being particularly suitable for welding or moulding. For example, suitable films include American Renolit Infuflex Barrier 9101 (SOLMED® BF 9101; American Ronolit Crop, La Porte, Ind., USA), American Renolit BF-1400 (SOLMED® BF-1400 Film; American Renolit Corp, La Porte, Ind., USA), American Renolit 4301 (SOLMED® Granuflex, American Renolit Crop, La Porte, Ind., USA), Mitos Durapure (Mitos Technologies, Phoenixville, Pa., USA) and MILLIPORE® Pureflex Process Container Film, (Millipore Corp, Billerica, Mass., USA).

The bag also comprises a chromatography medium filling port (16) through which dry or wet media or slurry is added to the bag (10). In the embodiment shown in FIG. 1b, the bag (10) has one compartment (11) for receipt of media (not shown) via port (16). Although not shown in FIG. 1a or 1b, the bag (10) also comprises a first and second end piece attached to the exterior wall (12) and adjacent to each of the distribution elements (13, 14), respectively. The end pieces are made from a rigid or semi-rigid material that prevents seepage of carrier liquid from the bag (10) and has openings for receipt of an inlet (25) and outlet (26) for carrier liquid. In one embodiment, the opening takes the form of a resilient septum (not shown) which receives the inlet (25) or outlet (26) for carrier liquid. Suitable materials for the production of the end pieces include inert metals and plastics such as polypropylene. Preferably the end piece is welded or moulded to the exterior wall (12).

In one embodiment (not shown) the end piece and the distribution element may be integrated into a single unit; suitable materials may include semi-flexible plastics such as polypropylene. The unit can be prepared by machining or moulding.

The use of rigid or semi-rigid materials in the component parts of the bag allows for the formation or compression of the packed bed. Preferably, the bag and its component parts are fabricated from biologically and chemically inert materials which are approved by regulatory authorities, such as the US Food and Drug Administration, for the manufacture of drugs.

The bag (10) may also comprise a second compartment (17), adjacent to the first compartment (11) of the bag (10) which acts as a hydraulic chamber to compress the first compartment (11) as described below. In other embodiments, the second compartment (17) may be a separate bag adjacent to the first compartment (11) which acts as a hydraulic chamber.

In FIGS. 1a and 1b, the bag (10) is enclosed by the column (20) housing (22) and lid (21), at least one of these components being semi-rigid or rigid. The bag (10) is filled with a dry powder or wet slurry of chromatography media through port 16. The column (20) may be sterilised by gamma irradiation on filling with media prior to use, or alternatively the bag may be sterilised by gamma irradiation or autoclaving on charging with media, and then stored or shipped to a user.

To prepare the media bed for chromatographic separation, a user will insert the the bag (10) into a chamber of a chromatography column (20), close the column housing (22) and lid (21) such that walls of the bag (10) fit tightly within the chamber and, in one embodiment, use the flow packing method to compress the bed (not shown). The packed column could then also be sterilised by gamma radiation prior to use.

In another embodiment, the second compartment or hydraulic chamber (17) can be filled with hydraulic fluid via port (24) to axially compress the first compartment (11) of the bag (10) containing media in order to maintain bed stability.

Alternatively, the first compartment (11) can be compressed mechanically by a piston or adapter present in the column chamber.

Separation of chemical compounds, such as proteins, may now occur by flowing a carrier liquid containing the compounds into the bag 10 (via inlet 25) and through the chromatographic media, the eluant being collected at outlet 26. Alternatively, the carrier flow can be reversed, such that port 26 serves as an inlet and eluant is collected at port 25.

In another embodiment, the user will insert the bag (10) into a chamber of an axial chromatography column (20), close the column housing (22) and lid (21) such that the bag is confined by the rigid housing and arrange the column in a vertical direction to apply liquid to the bag such that a consolidated bed is formed. When forming the consolidated bed by application of flow in downward direction, a gap may be formed above the consolidated bed.

In another embodiment, the walls of the bag will be displaced to reduce said gap formed above the consolidated bed in order to reduce the hold-up volume of column and/or to mechanically stabilise the consolidated bed.

In use, a liquid sample containing a chemical (such as a protein, peptide, antibody, nucleic acid or mixtures thereof) or a cell (or cellular mixture) is loaded onto the consolidated bed and allowed to equilibrate. The bag is then removed from the column and may be stored at low temperature (e.g. −20° C.) to minimise chemical or cellular loss or breakdown due to chemical, photochemical or biological instability. Alternatively, the bag may be transported at low temperature (such as, for example, −20° C.) to another location. Following storage and/or transport at low temperature, the bag may be equilibrated to an operating temperature at or above 4° C., placed in a semi rigid or rigid column and the chemical or cell eluted from the chromatographic medium. Alternatively, the chemical or cell which is loaded on the chromatographic medium may be subjected to processing, such as a chemical or biological reaction, following equilibration and replacement of the bag in the rigid or semi-rigid column at temperatures at or above 4° C. The product of the processing step may then be eluted from the column.

In one embodiment, the axial column of FIG. 1 is designed in a cylindrical shape. In another embodiment, the axial column is designed having a cross-sectional shape deviating from a circle found at the cylindrical shape, such as being of oval or rectangular shape. The shape of the rigid housing confining the column is adapted accordingly. For example, the column could be made to adopt to the shape of a 2 D pillow bag or a 3D rectangular bag that has been fitted with suitable distribution systems at inlet and outlet side. In yet another embodiment, the cross section of the column and bag may vary across the axial position in between the end pieces as being rectangular or oval at the end pieces and being circular or oval in the middle of the column, for example.

In another embodiment, the rigid housing is opened and closed at the side of the column and housing instead of having a removable lid as depicted in FIG. 1. In yet another embodiment, the rigid housing consists of two or more wall segments mounted together after having inserted the bag.

FIGS. 2a, b and c are schematic sectional plan views of a bag (210) in accordance to the invention which can be packed by radial compression. The bag (210) is tubular in nature with a hollow core or centre (230). In the embodiment shown, the exterior (212) and interior (219) walls of the bag (210) have welded opposed liquid distribution elements (213, 214) which allow passage of carrier liquid from the exterior to the interior of the bag (or in the reverse direction depending upon the direction of flow). In the embodiment shown, the bag (210) has semi-rigid walls (222) which can exert a radial, compressive force against the walls (212, 219) of the bag (210). The outer or exterior wall (212) of the bag has indents (215) which allow mild compression of the media filled bag (210) in response to the radial force of the semi-rigid walls (222). The bag (210) is stable under such mild compression and may be stored or transported to a user (FIG. 2a).

Bed packing is achieved by applying a radial mechanical compression to the walls (222) of the bag (210) as indicated by the arrows in FIG. 2b. As can be seen in FIG. 2c, the radial forces exerted on the bag (210) closes the indents (215) and is transmitted through the bag, compressing the media within.

In another embodiment, mild compression of bed is achieved using the flow packing method described above.

FIGS. 3a, b and c show the component parts of a radial column using a bag 310 according to the invention. FIG. 3a illustrates a cylindrical rigid core (340) with a stand (342) and locking lid (344). The lid 344 has apertures or connectors to accommodate an outlet port (346) for eluant and a media filling port (348). FIG. 3b depicts an outer cylindrical shell (350), typically composed of a semi rigid plastic sheet (351), which can wrapped around the radial flow bag 310 shown in FIG. 3c and used to radially compress it. In the embodiment shown, the length of the sheet (351) is greater than the external circumference of the bag 310 such that there is an overlap 354 to allow for changes in the diameter of the sheet (351) during compression. Other functional designs, such as pleating of the sheet, are also possible to achieve this purpose. The shell (350) has an aperture or connector (352) to accommodate a carrier liquid inlet (325).

FIG. 3c illustrates a bag (310) according to the invention. The bag has a tubular configuration with a hollow core 330. A first liquid distribution element (313) and second liquid distribution element (314) are welded to the exterior (312) and interior (319) walls of the bag (310), respectively. A media inlet port (316) is used to fill the bag with media, typically in the form of a slurry, as indicated by the arrow in FIG. 3c. Carrier liquid enters the bag via inlet 325, flows through the media bed (not shown) and exits via outlet (326, see arrows).

A radial flow column (360) is prepared by inserting the bag (310) over the rigid core (340), wrapping the cylindrical shell (350) around the exterior wall of the bag, and locking the lid (344) into position (FIG. 3d). The bag is filled with media slurry via inlet port 316 and excess media removed via outlet 326 or 325, prior to sealing the inlet port (316). The media in the bag may then be equilibrated with carrier liquid which will enter the column via inlet 325 and exit via port 326. In one embodiment, the bed is compressed by the flow packing method describe above.

In another embodiment, the outer shell (350) is radially compressed to form a packed bed of chromatography media in the bag. Radial compression can be effected in a number of ways, such as pulling the overlap 354 to constrict and compress the bag against the rigid core (FIG. 3e). Other means for compression are possible, such as clamping or tightening radial bands. Once the outer shell 350 has been compressed it is secured in position to stabilise the packed bed of media (for example, by use of tie bands 370). The column is now ready to be used for chromatographic separation of chemicals, such as proteins and/or peptides. The sample containing the chemical(s) to be separated or purified are dissolved in carrier liquid and applied to the column. The carrier liquid enters the bag via inlet 325 and first distribution element 313, partitions over the media bed (not shown) where separation occurs and passes through the second element 314 to exit the column at outlet port 326. It will be understood, that the column may be run in the reverse direction by reversing the direction of flow.

Low Temperature Storage Experiments

The experiments detailed below are described fully in Applicant's U.S. patent application 61/370,878 entitled "Stabilization and Storage Media and Method", filed on 5 Aug. 2010. Where national law permits, the content is hereby incorporated by reference in its entirety herein as if it had been specifically incorporated.

It is generally known that the storage of proteins (e.g. antibodies) in solution leads to aggregation over time. By freezing the protein solutions in a carefully designed buffer environment at slow and controlled rates of freezing aggregation can be reduced, but the aggregate content will inevitably be higher after storage. Experiments were then performed using an alternative storage approach by using different gel media to bind or encapsulate the target proteins.

Storage of Human Polyclonal IgG with a Low Initial Dimer Content in Solution or on Gel Media The monomer fraction of human polyclonal IgG (1% dimer) was first concentrated to 121.5 AU (A280 nm) using VIVASPIN® 6 ultrafiltration units and filtered with 0.2 .mu.m syringe filters. Various experimental capture storage hydrogel media, and control (noncapture SEC) media (see Materials above) were dispensed into 96 well filter plates (MULTITRAP® plates). The MULTITRAP® protocol was followed using the concentrated monomer fraction of human polyclonal IgG as antibody sample. In parallel, antibody samples were mixed with the various buffers used for the different "gel media" for subsequent storage in solution at −20° C. 6.7 .mu.l antibody solution was mixed with 13.3 .mu.l of each buffer respectively.

Buffers used for samples and equilibration/washing of gel media were typical adsorption capture buffers for the different media used:

"pH 5 IEX"=20 mM Na-Acetate, 0.02% (w/v) Na-azide, pH 5.0

"pH 9 IEX"=20 mM Na-Glycine, 0.02% (w/v) Na-azide, pH 9.0

"PBS"=10 mM Na-Phosphate, 2.7 mM KCl, 0.14M NaCl, 0.02% (w/v) Na-azide, pH 7.4

"pH 5 HIC"=25 mM Na-Acetate, 0.5 mM EDTA, 0.75M (NH4)2SO4, pH 5.0

The various chromatography gel media were stored in the 96-well MULTITRAP™ plate. The MULTITRAP® plates were stored in the fridge for 4 weeks at 4-8° C. (the protocol incubation time), whereas the antibody samples in solution were stored at −20° C. for 4 weeks including 6 freeze/thaw cycles. All samples were run in triplicate except for three of the anion exchange gel media, CAPTO™ Q, Q SEPHAROSE® FF and Q SEPHORASE® XL, that were run as single samples. After incubation or storage for 4 weeks, either the non-bound antibodies (flow-through) were collected (gel filtration SEC media SEPHADEX® G-50 and SUPERDEX® 200) or the bound and then eluted antibodies (all media except gel filtration media). Elution and strip buffers used were:

elution buffer: "3.3.times.PBS"=30 mM Na-Phosphate, 8.1 mM KCl, 0.42 M NaCl, pH 7.4 (for those samples of which buffers used for samples and equilibration/washing of gel media were "pH 5 IEX" and "pH 9 IEX");

elution buffer: 0.1 M Na-Glycine pH 2.9 (for those samples of which buffers used for samples and equilibration/washing of gel media were "PBS");

elution and strip buffer: 20 mM Tris-HCl pH 7.5 (for those samples of which buffers used for samples and equilibration/washing of gel media were "pH 5 HIC");

strip buffer: 10 mM NaOH, 1M NaCl for those samples of which buffers used for samples and equilibration/washing of gel media were ("pH 5 IEX" and "pH 5 HIC");

strip buffer: 0.5M Acetic acid (for those samples of which buffers used for samples and equilibration/washing of gel media were "PBS" and "pH 9 IEX")

Elution was performed in two steps, first with elution buffers and secondly with strip buffers. The latter are typically in bioprocessing used to remove any residual protein not eluted by the elution buffers—and to prepare column for possible additional use. Both elution fractions for each sample were analyzed respectively. All samples, stored in solution, on SEC control media or on binding media, were analyzed by SEC. The results are shown in Tables 1A-1D.

TABLE 1A

Dimer content in eluted fractions from human polyclonal IgG stored on gel media at 4-8° C. or frozen in solution at −20° C. for 4 weeks in pH 5 "IEX" buffer (20 mM Na-Acetate, 0.02% (w/v) Na-azide, pH 5.0).

| | % dimer | replicate | comment |
|---|---|---|---|
| Gel media | | | |
| CAPTO ™ MMC | 1.72 | 1 | |
| CAPTO ™ MMC | 0.84 | 2 | |
| CAPTO ™ MMC | 0.75 | 3 | |
| CAPTO ™ S | 2.95 | 1 | |
| CAPTO ™ S | 2.53 | 2 | |
| CAPTO ™ S | 1.68 | 3 | |
| SP SEPHAROSE ™ FF | 2.68 | 1 | |
| SP SEPHAROSE ™ FF | 2.21 | 2 | |
| SP SEPHAROSE ™ FF | 2.58 | 3 | |
| SP XL | 2.44 | 1 | |
| SP XL | 1.84 | 2 | |
| SP XL | 1.72 | 3 | |
| Storage in solution (−20° C.) | | | |
| pH 5 "IEX" | 3.41 | 1 | |
| pH 5 "IEX" | 3.23 | 2 | |
| pH 5 "IEX" | 3.92 | 3 | |

All samples stored on these gel media contained less antibody dimer content compared with storing the samples in solution at −20.degree. C. The start material contained 1.0% dimer and two of the replicates using CAPTO™ MMC as storing gel media contained less dimer than this initial dimer content level.

TABLE 1B

Dimer content in eluted fractions from human polyclonal IgG stored on gel media at 4-8° C. or frozen in solution at −20° C. for 4 weeks in "PBS" buffer (10 mM Na-Phosphate, 2.7 mM KCl, 0.14M NaCl, 0.02% Na-azide, pH 7.4).

| | % dimer | replicate | comment |
|---|---|---|---|
| Gel media | | | |
| nProtein A SEPHAROSE ™ 4 FF | 0.31 | 1 | |
| nProtein A SEPHAROSE ™ 4 FF | 0.30 | 2 | * <0.3, difficult to integrate peaks |
| nProtein A SEPHAROSE ™ 4 FF | 0.30 | 3 | * <0.3, difficult to integrate peaks |
| MABSELECT ™ | 0.52 | 1 | |
| MABSELECT ™ | 0.50 | 2 | * <0.5, difficult to integrate peaks |
| MABSELECT ™ | 0.50 | 3 | * <0.5, difficult to integrate peaks |
| SUPERDEX ™ 200 | 4.25 | 1 | |
| SUPERDEX ™ 200 | 4.54 | 2 | |
| SUPERDEX ™ 200 | 4.14 | 3 | |
| SEPHADEX ™ G-50 | 4.93 | 1 | |
| SEPHADEX ™ G-50 | 5.18 | 2 | |
| SEPHADEX ™ G-50 | 4.94 | 3 | |
| Storage in solution (−20° C.) | | | |
| PBS, pH 7.4 | 3.24 | 1 | |
| PBS, pH 7.4 | 3.27 | 2 | |
| PBS, pH 7.4 | 3.00 | 3 | |

Samples stored on the affinity gel media contained less antibody dimer compared with storing the samples in solution at −20° C. However, storage on noncapture SEC media resulted in higher levels of dimer. The start material contained 1.0% dimer and using nProtein A or MABSELECT™ as storing gel media resulted in less dimer content than the initial dimer content.

TABLE 1C

Dimer content in eluted fractions from human polyclonal IgG stored on gel media at 4-8° C. or frozen in solution at −20° C. for 4 weeks in "pH 5 HIC" buffer (25 mM Na-Acetate, 0.5 mM EDTA, 0.75M (NH4)2SO4, pH 5.0).

| | % dimer | replicate | comment |
|---|---|---|---|
| Gel media | | | |
| Butyl SEPHAROSE ™ HP | 1.31 | 1 | |
| Butyl SEPHAROSE ™ HP | 1.05 | 2 | |
| Butyl SEPHAROSE ™ HP | 1.25 | 3 | |
| CAPTO ™ Phenyl high sub. | 0.10 | 1 | |
| CAPTO ™ Phenyl high sub. | 0.10 | 2 | * <0.1 |
| CAPTO ™ Phenyl high sub. | 0.00 | 3 | * <0.1 |
| pH HIC 2% | | | poor binding of sample at 0.75M AmSO |
| pH HIC 2% | | | poor binding of sample at 0.75M AmSO |
| pH HIC 2% | | | poor binding of sample at 0.75M AmSO |
| pH HIC 4% AMBN | | | poor binding of sample at 0.75M AmSO |
| pH HIC 4% AMBN | | | poor binding of sample at 0.75M AmSO |
| pH HIC 4% AMBN | | | poor binding of sample at 0.75M AmSO |
| SEPHAROSE ™ HP 16% AMBN | | | poor binding of sample at 0.75M AmSO |
| SEPHAROSE ™ HP 16% AMBN | | | poor binding of sample at 0.75M AmSO |
| SEPHAROSE ™ HP 16% AMBN | | | poor binding of sample at 0.75M AmSO |
| CAPTO ™ Phenyl low sub. | 1.15 | 1 | |
| CAPTO ™ Phenyl low sub. | 0.87 | 2 | |
| CAPTO ™ Phenyl low sub. | 1.26 | 3 | |
| SEPHAROSE ™ HP 16% AMBN | | | poor binding of sample at 0.75M AmSO |
| SEPHAROSE ™ HP 16% AMBN | | | poor binding of sample at 0.75M AmSO |
| SEPHAROSE ™ HP 16% AMBN | | | poor binding of sample at 0.75M AmSO |
| Storage in solution (−20° C.) | | | |
| pH 5 "HIC" | 1.55 | 1 | |
| pH 5 "HIC" | 1.74 | 2 | |
| pH 5 "HIC" | 1.69 | 3 | |

The overall recoveries from the HIC gel media were poor, probably due to poor binding of the antibodies due to using too low a conductivity (salt concentration) in the adsorption buffer. To promote binding to the HIC gel media a higher concentration of (NH4) 2SO4 was needed. The results that were obtained showed that binding to the gel media gives less dimer during storage compared with storage in solution and for CAPTO® Phenyl high substitution (higher ligand concentration) media the dimer content was less than 1.0% (level in the start material).

TABLE 1D

Dimer content in eluted fractions from human polyclonal IgG stored on gel media at 4-8.degree. C. or frozen in solution at −20° C. for 4 weeks in "pH 9 IEX" buffer (20 mM Na-Glycine, 0.02% (w/v) Na-azide, pH 9.0).

| | % dimer | replicate | comment |
|---|---|---|---|
| Gel media | | | |
| CAPTO ™ Adhere | 0.69 | 1 | |
| CAPTO ™ Adhere | 0.95 | 2 | |
| CAPTO ™ Adhere | 0.75 | 3 | |
| CAPTO ™ Q | 2.27 | 1 | |
| CAPTO ™ Q | | | no sample |
| CAPTO ™ Q | | | no sample |
| Q SEPHAROSE ™ FF | 3.84 | 1 | |
| Q SEPHAROSE ™ FF | | | no sample |
| Q SEPHAROSE ™ FF | | | no sample |
| Q XL | 3.31 | 1 | |
| Q XL | | | no sample |
| Q XL | | | no sample |
| Storage in solution (−20° C.) | | | |
| pH 9"IEX | 3.39 | 1 | |
| pH 9"IEX | 3.35 | 2 | |
| pH 9"IEX | 3.58 | 3 | |

Samples stored on CAPTO® Adhere gel media contained less antibody dimer content compared with storing the samples in solution at −20.degree. C. The dimer content was less than 1.0% as found in the start material. Storage on the other gel media resulted in about the same levels of dimeric proteins as storage in solution.

Storage of human polyclonal IgG with a high initial dimer content in solution or on gel media Polyclonal human IgG (GAMMANORM® 165 mg/ml) was diluted to 30 mg/ml with following equilibration/wash buffers:
 20 mM Na-Acetate, 0.02% (w/v) Na-azide, pH 5.0
 20 mM Na-Glycine, 0.02% (w/v) Na-azide, pH 9.0
 10 mM Na-Phosphate, 2.7 mM KCl, 0.14M NaCl, 0.02% (w/v) Na-azide, pH 7.4
 50 mM Na-Acetate, 1 mM EDTA, 1.5M (NH4) 2SO4, pH 5.0

Some protein was precipitated upon mixing the antibody solution with the fourth buffer solution containing 1.5M (NH4) 2SO4. The absorbance of these start materials were measured (on clarified solutions):

| Sample buffer | A280 cm$^{-1}$ |
|---|---|
| 20 mM Na Acetate, 0.02% (w/v) Na azide, pH 5.0 | 40.6 |
| 20 mM Na Glycine, 0.02% (w/v) Na azide, pH 9.0 | 40.5 |
| 10 mM Na Phosphate, 2.7 mM KCl, 0.14M NaCl, 0.02% | 40.8 |
| 500 mM Na Acetate, 1 mM EDTA, 1.5M (NH$_4$)$_2$SO$_4$, pH 5.0 | 28.5 |

SPINTRAP® columns were filled with 40 .mu.l of following gel media (i.e. 200 .mu.l 20% gel slurry) and were equilibrated according to the SPINTRAP® protocol:
 CAPTO® MMC mixed mode media, 20 mM Na-Acetate, 0.02% (w/v) Na-azide, pH 5.0
 CAPTO® S cation exchange media, 20 mM Na-Acetate, 0.02% (w/v) Na-azide, pH 5.0
 CAPTO® Adhere mixed mode media, 20 mM Na-Glycine, 0.02% (w/v) Na-azide, pH 9.0
 CAPTO® Q anion exchange media, 20 mM Na-Glycine, 0.02% (w/v) Na-azide, pH 9.0
 MABSELECT®, affinity media, 10 mM Na-Phosphate, 2.7 mM KCl, 0.14M NaCl, 0.02% (w/v) Na-azide, pH 7.4
 SEPHADEX® G-50, control SEC media, 10 mM Na-Phosphate, 2.7 mM KCl, 0.14M NaCk, 0.02% (w/v) Na-azide, pH 7.4
 CAPTO® Phe hs, phenyl ligand containing HIC media, 50 mM Na-Acetate, 1 mM EDTA, 1.5M (NH$_4$)$_2$SO$_4$, pH 5.0
 pH HIC 6%, pH responsive polymer based HIC media, 50 mM Na-Acetate, 1 mM EDTA, 1.5M (NH$_4$)$_2$SO$_4$, pH 5.0
 pH HIC 16%, pH responsive polymer based HIC media, 50 mM Na-Acetate, 1 mM EDTA, 1.5M (NH$_4$)$_2$SO$_4$, pH 5.0

After equilibration, 40 µl of sample was added to each column (matching buffers). Three SPINTRAP™ columns of each gel media containing bound antibodies were stored at room temperature (+20° C.), in fridge (+4-8° C.) and in the freezer (−20° C.) respectively. In parallel, aliquots of antibodies in solution containing the various buffers were also stored at the same temperatures as the SPINTRAP® columns.

60 µl of matching buffer was added to all SPINTRAP™ columns after an incubation time of 24-26 days. The flow-through (non-binding fraction) was collected and the absorbance (A280 nm) was measured.

The various gel media was washed, then eluted with 400 µl of following elution buffers:
 CAPTO™ MMC, 20 mM Na-Phosphate, 1M NaCl, pH 7.0
 CAPTO™ S, 20 mM Na-Phosphate, 1M NaCl, pH 7.0
 CAPTO™ Adhere, 0.5M Acetic acid
 CAPTO™ Q, 20 mM Na-Phosphate, 1M NaCl, pH 7.0
 MABSELECT™, 0.5M Acetic acid
 SEPHADEX™ G-50, not eluted, flow-through fraction collected
 CAPTO™ Phe hs, 20 mM Na-Phosphate, 1M NaCl, pH 7.0
 pH HIC 6%, 20 mM Na-Phosphate, 1M NaCl, pH 7.0
 pH HIC 16%, 20 mM Na-Phosphate, 1M NaCl, pH 7.0

The absorbance (A280 nm) was measured on the eluted fractions. All samples from storage in solution and flow-through/elution fractions from the various gel media were analyzed by SEC. The antibody recovery and the dimer content are summarized in Table's 2A-4D.

TABLE 2A

Antibody recovery and dimer content in eluted fractions after storage of human polyclonal IgG on gel media or in solution. Buffer for storage: 20 mM Na-Acetate, 0.02% (w/v) Na-azide, pH 5.0. Initial dimer content directly after dilution was 16.9%.

| | Temp. °C | % dimer after 3.5 weeks | Total protein recovery % | Monomer IgG recovery % |
|---|---|---|---|---|
| Storage on gel media | | | | |
| CAPTO™ MMC 20 mM Acetate pH 5.0 | 20 | 8.0 | 24 | 27 |
| | 5 | 11.1 | 71 | 82 |
| | -20 | 10.7 | 76 | 87 |
| CAPTO™ S 20 mM Acetate pH 5.0 | 20 | 6.4 | 87 | 98 |
| | 5 | 8.5 | 93 | 108 |
| | -20 | 8.3 | 88 | 101 |
| In solution storage | | | | |
| 20 mM Acetate pH 5.0 | 20 | 11.6 | | |
| | 5 | 13.8 | | |
| | -20 | 13.0 | | |

Storage on CAPTO™ S results in much reduced dimer content and the antibody recovery is high. CAPTO™ MMC gives slightly lower dimer content after storage compared with storage in solution with good recoveries at lower temperatures.

TABLE 2B

Antibody recovery and dimer content in eluted fractions after storage of human polyclonal IgG on gel media or in solution. Buffer for storage: 20 mM Na-Glycine, 0.02% (w/v) Na-azide, pH 9.0. Initial dimer content directly after dilution was 24.4%.

| | Temp. °C | % dimer after 3.5 weeks | Total protein recovery % | Monomer IgG recovery % |
|---|---|---|---|---|
| Storage on gel media | | | | |
| CAPTO™ Adhere 20 mM Glycine pH 9 | 20 | 4.0 | 88 | 111 |
| | 5 | 1.5 | 93 | 122 |
| | -20 | 2.0 | 93 | 109 |
| CAPTO™ Q 20 mM Glycine pH 9 | 20 | 7.4 | 72 | 91 |
| | 5 | 9.0 | 57 | 74 |
| | -20 | 7.5 | 66 | 77 |
| In solution storage | | | | |
| 20 mM Glycine pH 9 | 20 | 20.9 | | |
| | 5 | 23.5 | | |
| | -20 | 14.5 | | |

Storage on CAPTO™ Adhere gives much improved results compared with storage in solution. The recoveries are very high with possible conversion of dimers into monomers as evidenced by the higher than 100% recovery of monomer IgG. Results from storage on CAPTO™ Q show less dimer content compared with storage in solution, but the recoveries were less than 80%.

TABLE 2C

Human polyclonal IgG antibody recovery and dimer content in eluted fractions after storage. Buffer for storage: 10 mM Na-Phosphate, 2.7 mM KCl, 0.14M NaCl, 0.02% (w/v) Na-azide, pH 7.4. Initial dimer content directly after dilution was 24.6%

| | Temp. °C | % dimer after 3.5 weeks | Total protein recovery % | Monomer IgG recovery % |
|---|---|---|---|---|
| Storage on gel media | | | | |
| MABSELECT™ PBS, pH 7.4 | 20 | 1.7 | 88 | 108 |
| | 5 | 2.2 | 89 | 115 |
| | -20 | 2.1 | 90 | 116 |
| SEPHADEX™ PBS, pH 7.4 | 20 | 14.4 | 98 | 120 |
| | 5 | 17.0 | 73 | 94 |
| | -20 | 14.4 | 97 | 125 |
| In solution storage | | | | |
| PBS, pH 7.4 | 20 | 18.3 | | |
| | 5 | 22.4 | | |
| | -20 | 22.3 | | |

Storage on MABSELECT™ gives much improved results compared with storage in solution. The recoveries are very high with possible conversion of dimers into monomers evidenced by the higher than 100% recovery of monomer IgG. Results from storage on SEPHADEX™ G-50 show slightly less dimer content compared with storage in solution but have the highest protein recovery of all gel media perhaps due to the non-binding properties.

TABLE 2D

Human polyclonal IgG antibody recovery and dimer content in eluted fractions after storage. Buffer for storage: 50 mM Na-Acetate, 1 mM EDTA, 1.5M $(NH_4)_2SO_4$, pH 5.0. Initial dimer content directly after dilution was not measured due to precipitation.

| Storage on gel media | Temp. °C | % dimer after 3.5 weeks | Total protein recovery % | Monomer IgG recovery % |
|---|---|---|---|---|
| CAPTO™ Phe hs | 20 | 6.5 | 31 | |
| | 5 | 5.7 | 49 | |
| | -20 | 7.7 | 57 | |
| pH HIC 16% | 20 | 5.9 | 70 | |
| | 5 | 6.9 | 79 | |
| | -20 | 9.0 | 68 | |
| pH HIC 6% | 20 | 5.7 | 68 | |
| | 5 | 7.4 | 80 | |
| | -20 | 8.2 | 82 | |

For HIC gel media, there was no starting material for comparison due to target precipitation. The absorbance (A280 nm) of the start material was 28.5 AU compared with over 40 AU for the other start materials. The protein recovery after clarification was good for pH HIC 6% and pH HIC 16% gel media. Compared with other gel media, the dimer content after storage was in the low range, showing a positive effect on aggregation stabilization or reduction.

Figure 4A:
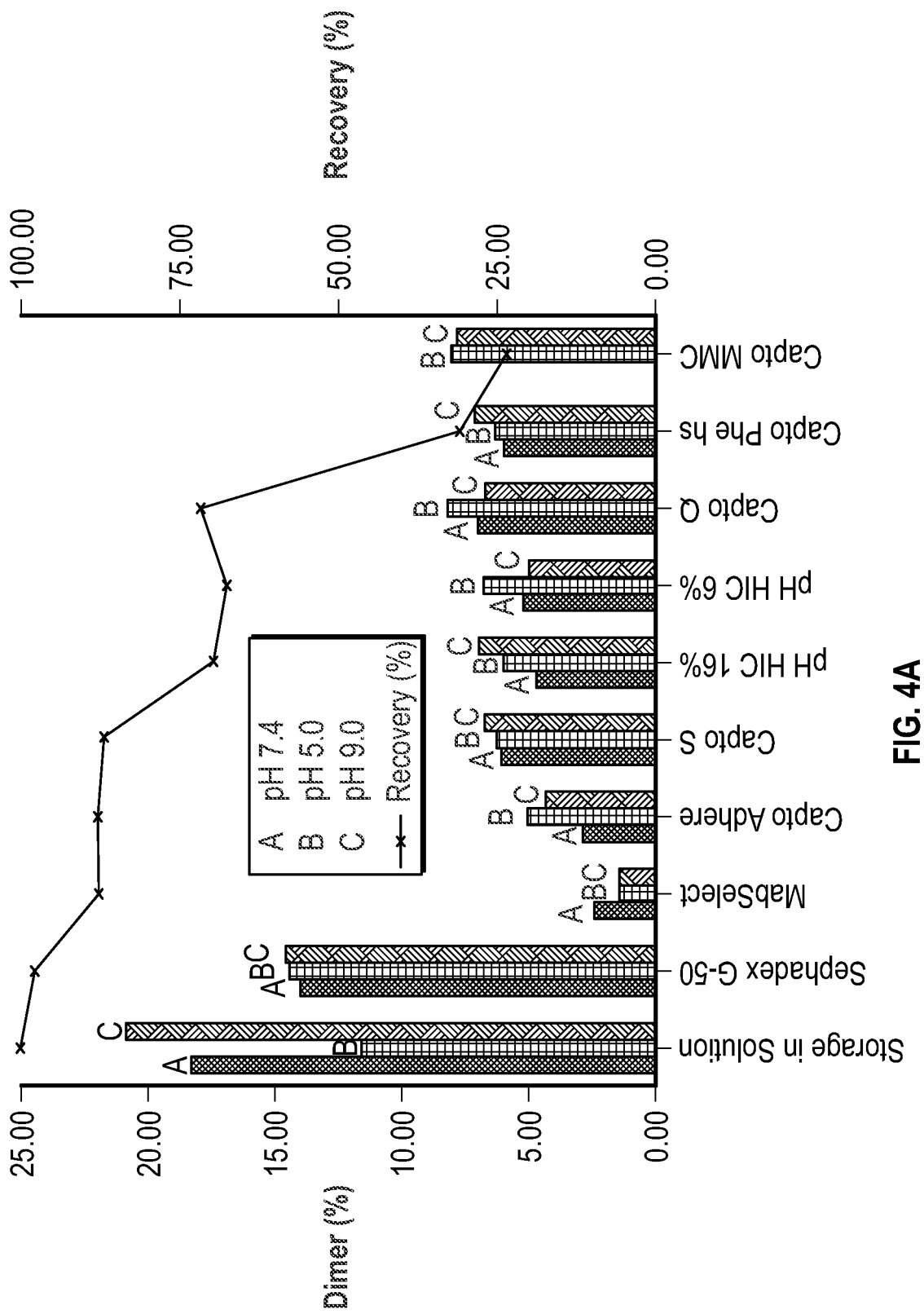
FIGS. 4a, b and c show results from low temperature storage experiments with pH 7.4, 5.0, and 9.0 respectively.
Figure 4B:
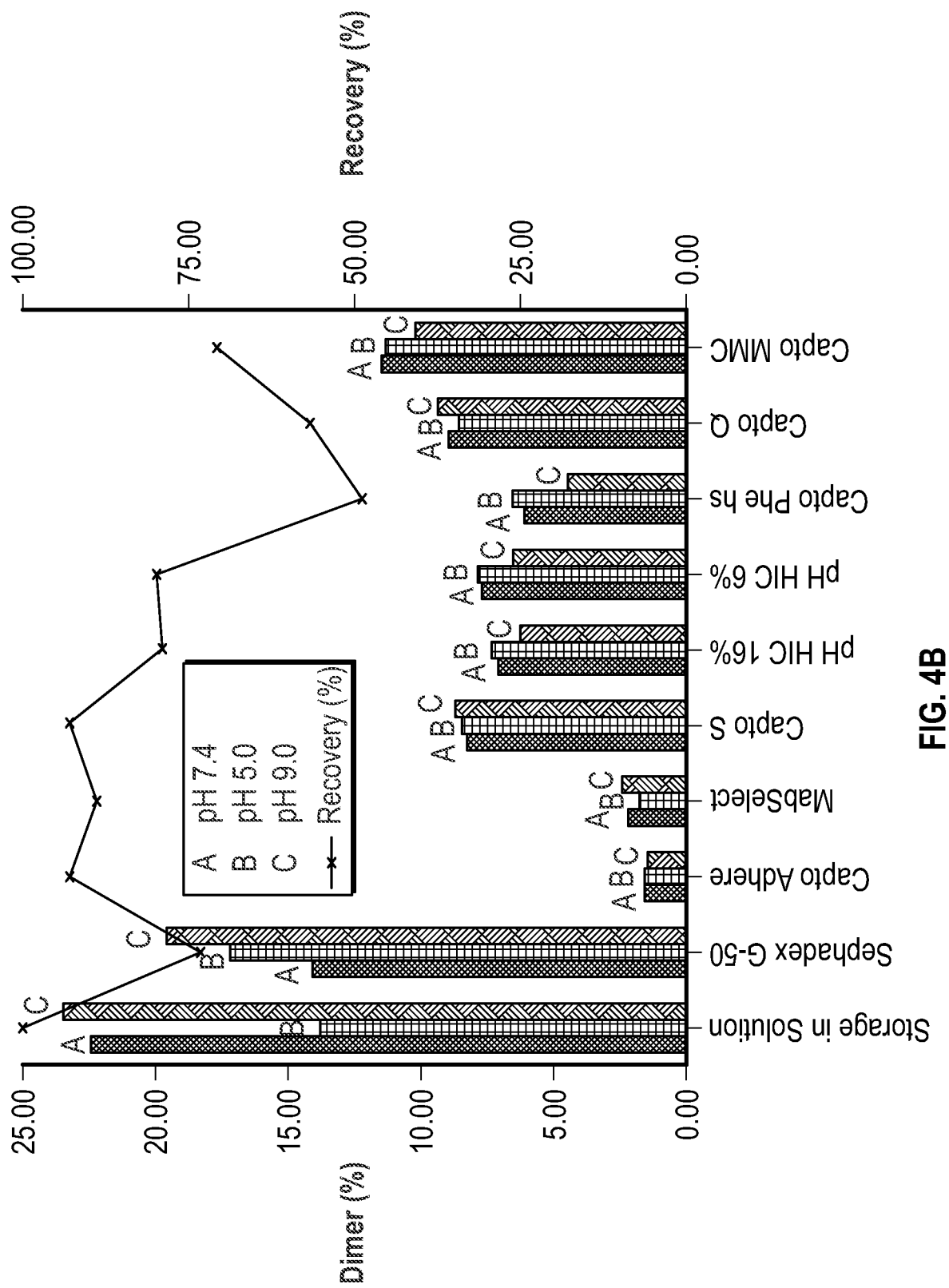
Figure 4C:
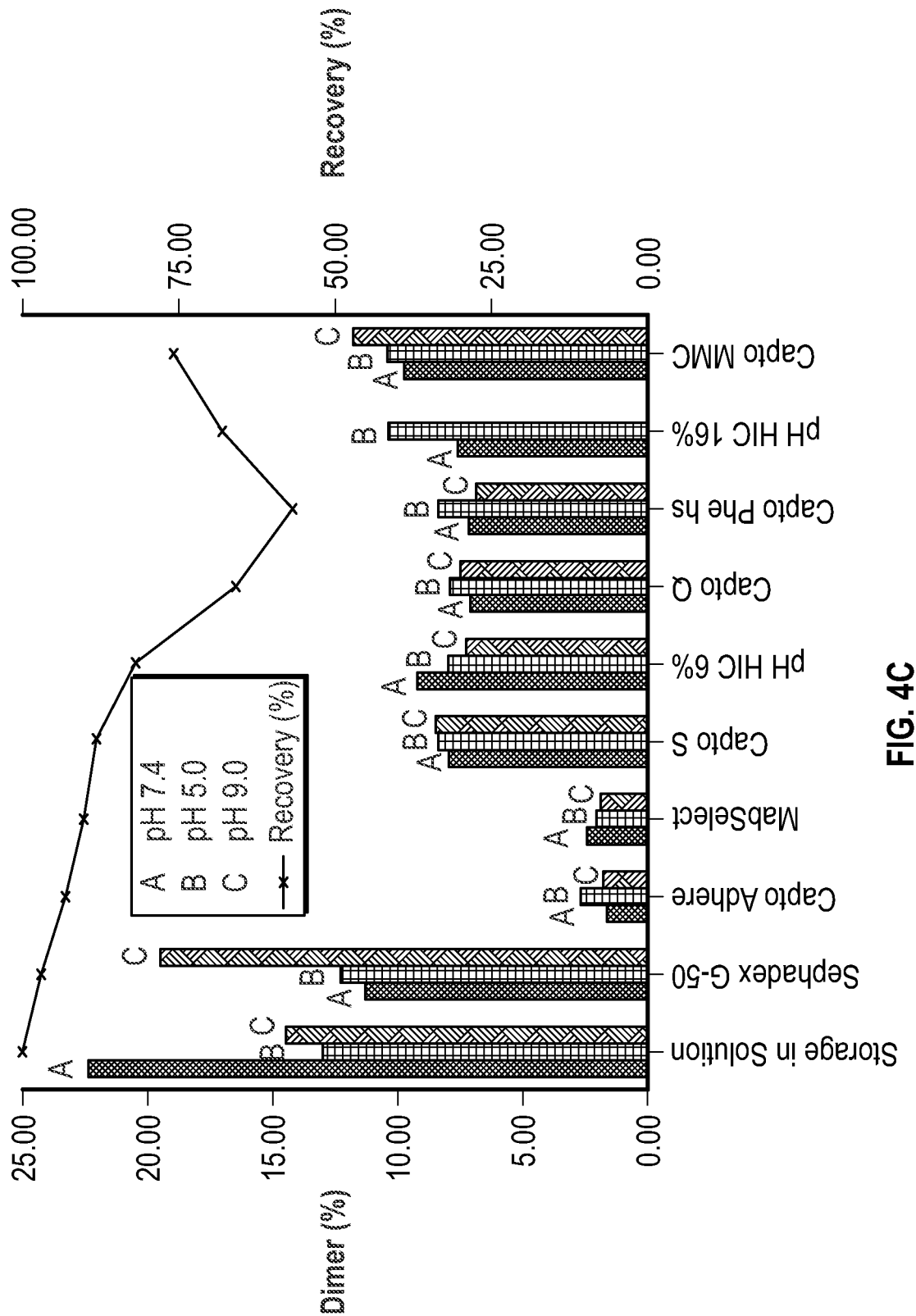

The results for all storage conditions are shown as graphs in FIGS. 4A-C. Storage on CAPTO™ Adhere or on MABSELECT™ shows very low levels of dimers or aggregates with high recoveries of monomer IgG after storage, reflecting apparent ability of the media to reduce dimer levels during storage. Storage on CAPTO™ Adhere or on MABSELECT™ shows very low levels of dimers or aggregates with high recoveries of monomer IgG after storage, reflecting apparent ability of the media to reduce dimer levels during storage.

The initial dimer content directly after dilution of GAMMANORM® (165 mg/ml) was between 16.9-24.6% depending on buffer used. After storage for 3.5 weeks at different temperatures, the dimer content was slightly lower in the various solutions.

The buffer composition, pH, salt content and type seem to affect the equilibrium faster and to a higher degree than compared with the protein concentration. Storage of GAMMANORM® in a low salt buffer at pH 5.0 results in much lower dimer content compared with storage at pH 7.4 or pH 9.0, both directly after dilution and after storage for 3.5 weeks.

The effect of temperature is less obvious.

The best storage condition for GAMMANORM® in solution seems to be storage in 20 mM Na-Acetate, 0.02% Na-azide pH 5.0 at +20° C. according to these experiments.

However, the most pronounced effect on dimer content was observed when storing antibodies on binding media. Especially on CAPTO™. Adhere and MABSELECT™, although storage on these gel media was done at pH 9.0 and pH 7.4 respectively. The effect was so great, that when calculating the recovery of monomeric IgG, the result was higher than 100% for samples stored on CAPTO™ Adhere and MABSELECT™ The total protein recovery was never higher than 98% though (SEPHADEX™ G-50, non-binding media).

Thus, storing on binding media may have several benefits including:
1. Stabilization of IgG against aggregation (slow down kinetics)
2. Removal of IgG dimer (polishing)
3. Promote monomer formation (reversal of monomer/dimer equilibrium)

Storing a start material with low initial dimer content on gel media would benefit from stabilization and polishing. Starting from high initial dimer content would also benefit from reducing the amount of dimers and increase the percent of monomers.

Results obtained from non-binding media show no or little reduction of dimer content. In the first experiment starting with low initial dimer content, the storage on non-binding gel media (SUPERDEX™ 200 and SEPHADEX™ G-50) resulted in slightly more dimers compared with storing in solution. Starting with high initial dimer content, the storage on SEPHADEX™ G-50 resulted in slightly less dimers compared with storage in solution. The overall dimer content was however always higher compared with storing on any capture gel media.

The skilled person will understand that flexible bags in accordance to the invention may be employed for the preparation of separation or reaction units that rely on introducing a particulate material into a column chamber and bringing the material into contact with a fluid as either a packed, expanded, consolidated or fluidized bed for achieving the separation or reaction process.

Whilst the present invention has been described in accordance with various aspects and preferred embodiments, it is to be understood that the scope of the invention is not considered to be limited solely thereto and that it is the Applicant's intention that all variants and equivalents thereof also fall within the scope of the appended claims.

What is claimed is:

1. A method of packing a chromatography column with a flexible bag configured for containing a chromatographic medium, wherein the chromatography column comprises a housing,
said method comprising the steps of
a. inserting the flexible bag containing a wet medium into the housing of the chromatography column, the flexible bag comprising:
an exterior wall of a non-porous material attached to both a first liquid distribution element and a second liquid distribution element at respective opposed ends of said exterior wall thereby defining an interior compartment for chromatographic medium therein, wherein said first liquid distribution element is facing said second liquid distribution element, the first liquid distribution element being welded or moulded to the exterior wall;
a medium filling port fluidically connected to the interior compartment for chromatographic medium; and
a first end piece and a second end piece attached to said bag exterior wall and adjacent to the first liquid distribution element and the second liquid distribution element respectively, the first end piece and the second end piece each comprising an opening for receipt of an inlet or an outlet for carrier liquid;
wherein the first liquid distribution element and the second liquid distribution element is each selected from the group consisting of filter, mesh, net, and sinter, and each of the first and second liquid distribution elements includes pores that are porous to liquids and do not allow the chromatographic medium to pass through into a chamber of the chromatography column;
b. closing the column housing; and
c. forming or compressing a packed bed or a consolidated bed or a fluidized bed in the interior compartment for chromatographic medium,
wherein the column housing is rigid and the packed bed is formed or compressed by axial compression of the interior compartment for chromatographic medium of the flexible bag, and
wherein a hydraulic chamber is disposed in an interior compartment of the chromatography column and the packed bed, the consolidated bed, or the fluidized bed is formed or compressed by filling said hydraulic chamber with a hydraulic fluid, wherein said hydraulic chamber is its own separate flexible bag.

2. The method of claim 1, wherein the consolidated bed or the fluidized bed is formed, the method additionally comprising the steps of:
a. loading a chemical or cell onto said consolidated bed or fluidized bed; and
b. removing said flexible bag containing the wet medium from said chamber of said chromatography column for storage and/or transport.

3. The method of claim 2, further comprising the step of returning the flexible bag containing the wet medium to the chromatography column and eluting said chemical or cell from said consolidated bed or fluidized bed.

4. The method of claim 2, wherein said chemical is selected from the group consisting of protein, antibody, peptide, oligopeptide, nucleic acid, oligonucleotide, RNA, DNA, oligosaccharide and polysaccharide.

* * * * *